United States Patent [19]
Setlak et al.

[11] Patent Number: 6,021,211
[45] Date of Patent: Feb. 1, 2000

[54] METHOD AND RELATED APPARATUS FOR FINGERPRINT INDEXING AND SEARCHING

[75] Inventors: Dale R. Setlak, Melbourne; John C. Schmitt, Indialantic; Mark E. Boss, West Melbourne, all of Fla.

[73] Assignee: AuthenTec, Inc., Melbourne, Fla.

[21] Appl. No.: 09/033,437

[22] Filed: Mar. 2, 1998

Related U.S. Application Data

[63] Continuation of application No. 08/589,064, Jan. 23, 1996.

[51] Int. Cl.⁷ ...................................................... G06K 9/00
[52] U.S. Cl. .................................... 382/124; 707/6; 707/7
[58] Field of Search .................................... 382/124–127, 382/226, 227, 116, 115; 707/6, 2, 7; 356/71; 396/15; 340/825.34; 283/68, 69, 78

[56] References Cited

U.S. PATENT DOCUMENTS

| | | | |
|---|---|---|---|
| 3,959,884 | 6/1976 | Jordan et al. | 33/1 BB |
| 4,156,230 | 5/1979 | Riganati et al. | 382/124 |
| 4,553,206 | 11/1985 | Smutek et al. | 364/300 |
| 4,607,384 | 8/1986 | Brooks | 382/4 |
| 4,956,870 | 9/1990 | Hara | 382/30 |
| 5,291,560 | 3/1994 | Daugman | 382/117 |
| 5,465,303 | 11/1995 | Levison et al. | 382/124 |
| 5,831,619 | 11/1998 | Nakagawa et al. | 345/419 |
| 5,850,466 | 12/1998 | Schott | 382/141 |

*Primary Examiner*—Leo H. Boudreau
*Assistant Examiner*—Brian P. Werner
*Attorney, Agent, or Firm*—Allen, Dyer, Doppelt, Milbrath & Gilchrist, P.A.

[57] ABSTRACT

A method for indexing and searching a plurality of reference fingerprints to determine if a sample fingerprint matches one of the reference fingerprints includes the steps of: determining respective index values for the reference fingerprints and the sample fingerprint based upon characteristics of the fingerprints and with the index values being generally evenly distributed and continuous over a relatively large population of individuals; selecting a first subset of the reference fingerprints having index values in a first range relative to the index value of the sample fingerprint; and comparing the sample fingerprint to each fingerprint of the first subset of reference fingerprints to thereby determine if there is a match between the sample fingerprint and one of the reference fingerprints and without comparing the sample fingerprint to all of the reference fingerprints. The step of determining index values for the reference fingerprints and the sample fingerprint preferably comprises determining same based upon ridge flow curvature of the fingerprints. The step of selecting the first subset of reference fingerprints preferably comprises selecting same based upon an expected confidence value for locating the sample fingerprint in the first subset. Apparatus aspects of the invention are also disclosed.

13 Claims, 10 Drawing Sheets

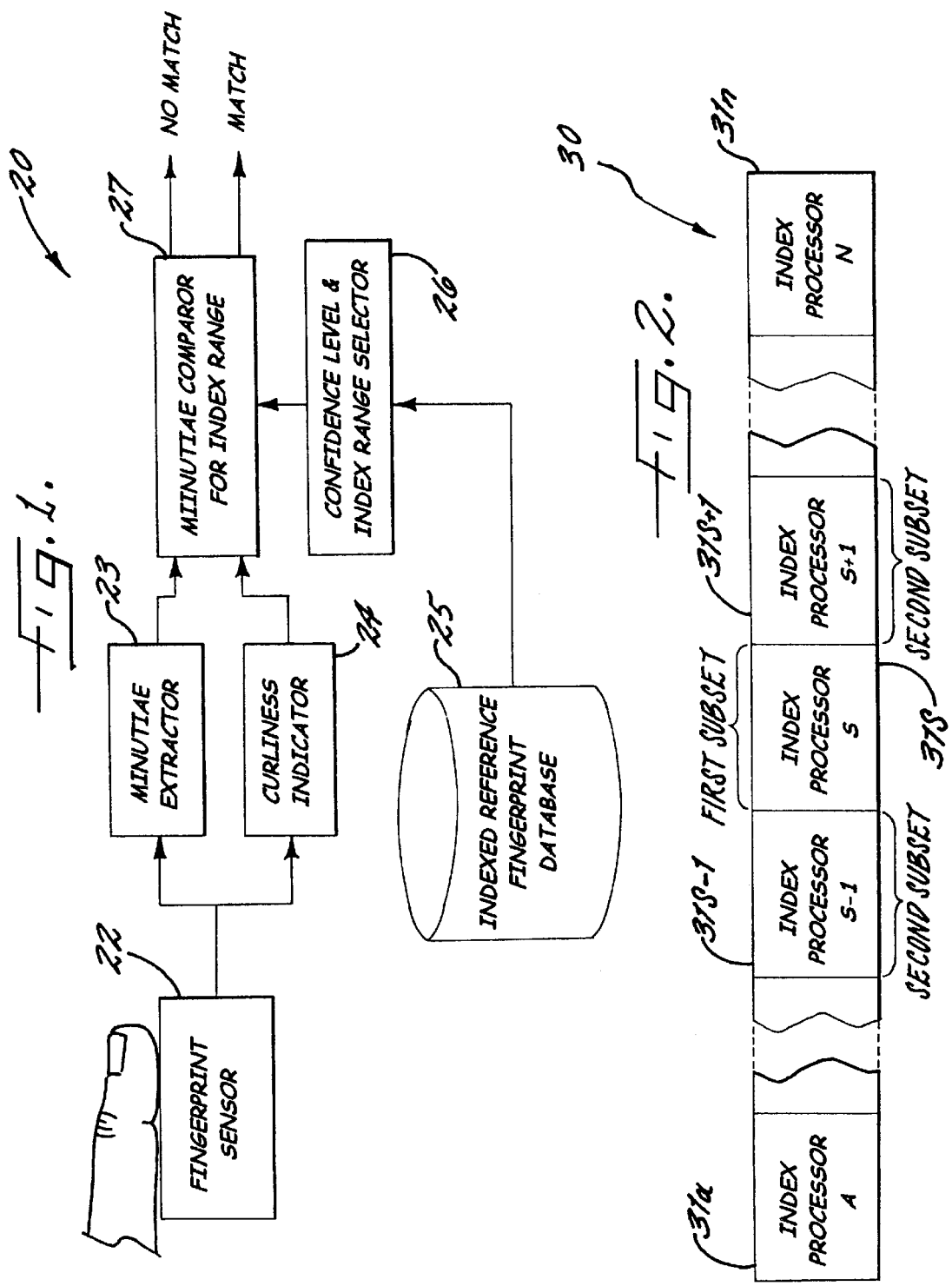

METHOD AND RELATED APPARATUS FOR FINGERPRINT INDEXING AND SEARCHING

This application is a continuation of Ser. No. 08/589,064 filed on Jan. 23, 1996.

FIELD OF THE INVENTION

The invention relates to the field of fingerprint processing, and, more particularly, to the field of efficiently searching for a fingerprint match in a relatively large database of fingerprints.

BACKGROUND OF THE INVENTION

Fingerprint matching is a reliable and widely used technique for personal identification or verification. In particular, a common approach to fingerprint identification involves scanning a sample fingerprint or an image thereof, converting it into electrical signals, and storing the image and/or unique characteristics of the fingerprint image. The characteristics of a sample fingerprint may be compared to information for reference fingerprints already in storage to determine identification or for verification purposes.

Unfortunately, comparing a sample fingerprint to a large number of reference fingerprints may be prohibitively expensive and/or simply take too long. Accordingly, fingerprints are typically classified into a plurality of discrete sets and/or subsets in the form of a hierarchical tree to thereby expedite searching. For example, a common top level classification for fingerprints usually differentiates the prints into the classes of: plain whorl, plain loop, tented arch, etc. based upon broad ridge pattern types. These classes may be yet further divided into subclasses. Accordingly, a fingerprint sample to be searched, once itself classified, can be more efficiently compared to only those prints in the respective classes and subclasses of the search tree. For example, U.S. Pat. No. 5,465,303 to Levison et al. describes both the widely used Henry classification system and the Vucetich classification system.

The conventional classification approaches may result in binning of fingerprint types or classifications, wherein a single bin is searched for the matching print. Unfortunately, the bins may still be relatively large thus resulting in lengthy and expensive searching. Moreover, a print is considered either in one bin or another and there is no consideration given to any uncertainty in whether the print is in one bin or another. In other words, there is typically no relation between adjacent bins that would assist in searching. Any degradation in this print quality may also result in it being simply in the wrong bin and thus unmatchable.

When the quality of the original copy of a fingerprint is bad, the print may contain many local distortions of the ridge pattern which may result in incorrect orientation of the fingerprint. U.S. Pat. No. 5,140,642 to Hsu et al. is directed to a method for determining the actual position of a core point of a fingerprint based upon finding ridge flows and assigning a direction code, correcting the ridge flows, and allocating the core point based upon the corrected direction codes. Along these lines, U.S. Pat. No. 5,040,224 to Hara discloses an approach to preprocessing fingerprints to correctly determine a position of the core of each fingerprint image for later matching by minutiae patterns.

Fingerprint minutiae, the branches or bifurcations and end points of the fingerprint ridges, are often used to determine a match between a sample print and a reference print database. For example, U.S. Pat. Nos. 3,859,633 and 3,893,080 both to Ho et al. are directed to fingerprint identification based upon fingerprint minutiae matching.

U.S. Pat. No. 3,959,884 to Jordan et al. discloses a method of classifying fingerprints by converting a fingerprint to a pattern of binary values which define a spatial array of ridges and valleys. A part of the pattern is selected for transformation by a repeatable criteria, such as a circular area having its center at the average center of curvature of the circular ridges of the upper part of the print. The data represented by the selected part is transformed into a plot of a relative position/intensity surface with a predetermined set of first and second coordinates and a variable third coordinate having a value dependent upon the frequency of occurrence of ridges when the origin of the first and second coordinates is taken at multiple positions over the selected area. The surface is divided into multiple areas, the number of areas being equal to the desired number of code elements in a descriptor code to be constructed. The curvature of the surface within each area is preferably quantized to produce the number of code elements. Finally, a descriptor code is constructed by concatenating the code elements in a predetermined order.

U.S. Pat. No. 4,151,512 to Riganati et al. describes a fingerprint classification method using extracted ridge contour data. The ridge flow in the fingerprint pattern and minutiae data are identified and extracted from a fingerprint pattern. Topological data, identifying singularity points such as tri-radii and cores, as well as ridge flow line tracings related to those points are extracted from the ridge contour data. The extracted information is used to automatically perform classification of the fingerprint patterns and/or matching of the fingerprint pattern with patterns stored in a mass file. Classification can be positively determined with a high degree of certainty or alternatively a priority listing of probable classification types can be determined when the classification is made with a low degree of certainty. Where a priority listing is produced, successive bins of the main file are searched in succession according to the priority listing of the probable classification types. When a particular classification type is selected, the extracted minutiae data is then compared with the minutiae data of each of the stored prints within the corresponding particular classification bin of the main file.

U.S. Pat. No. 4,185,270 to Fischer II et al. discloses a process for encoding and verification also based upon minutiae. U.S. Pat. No. 4,210,899 to Swonger et al. discloses an optical scanning fingerprint reader cooperating with a central processing station for a secure access application such as admitting a person to a location or provide access to a computer terminal. U.S. Pat. No. 4,525,859 to Bowles is also directed to minutiae matching and describes a system including, among other things, signal producing means for producing an electrical signal for each point on a matrix of points; and first, second and third determining means operating on subarrays of matrix points. U.S. Pat. No. 4,947,443 Costello discloses a method for verifying the identity of a person using four characteristics from among the six characteristics. The patent also discusses encoding a credit card, bank card, or other document with a code representing a person's fingerprint.

Yet another approach to fingerprint matching attempts to assign a unique digital code to each fingerprint. For example, U.S. Pat. No. 4,747,147 to Sparrow discloses a fingerprint scanning system and method for rotating a scan line about a central point on the fingerprint. A code representing the types of irregularities is recorded, along with a ridge count so that coordinates give a complete topological and spatial description of a fingerprint for computer processing.

Along these lines, U.S. Pat. No. 5,363,453 to Gagne et al. relates to a system and method for generating a 24 byte numeric fingerprint identifier so that the data may be included on a magnetic strip, for example. In addition, the background of the invention section describes a prior art device made by Fingermatrix which provided a 400 byte numeric identifier. The method does not rely on minutiae as many of the above described patents. However, the ability to accurately and repeatably assign a unique digital code to a fingerprint may be impractical given the relatively large number of fingerprints in typical databases and the quality of the prints therein.

Other approaches are also known for attempting to efficiently and accurately find a match between a sample fingerprint and a database of reference prints. For example, U.S. Pat. No. 5,239,590 to Yamamoto discloses a fingerprint image processing method wherein a master and a sample fingerprint image are divided into a plurality of blocks and each block is divided into a plurality of block areas, in turn, having a plurality of pixels with an associated direction. The direction of each pixel is determined based on pixel density partial differentials between the pixel and adjacent pixels for a plurality of directions. A match is determined based upon specific dispersion, mean, and cross-correlation calculations.

Despite a proliferation of attempted fingerprint classification and automated searching approaches, there still exists a need for reliable and efficient automated fingerprint data storage and matching.

SUMMARY OF THE INVENTION

In view of the foregoing background, it is therefore an object of the present invention to provide a method and apparatus for permitting efficient searching of a relatively large database of reference fingerprints.

It is another object of the present invention to provide a method and apparatus for permitting efficient searching of a relatively large database of fingerprints where some of the fingerprints may have degraded quality.

These and other objects, advantages and features in accordance with the present invention are provided by a method for indexing and searching a plurality of reference fingerprints to determine if a sample fingerprint matches one of the reference fingerprints. In one embodiment, the method preferably comprises the steps of: determining respective index values for the reference fingerprints and the sample fingerprint based upon characteristics of the fingerprints and with the index values being generally evenly distributed and continuous over a relatively large population of individuals; selecting a first subset of the reference fingerprints having index values within a first range relative to the index value of the sample fingerprint; and comparing the sample fingerprint to each fingerprint of the first subset of reference fingerprints to thereby determine if there is a match between the sample fingerprint and one of the reference fingerprints. Accordingly, the sample fingerprint need not be compared to all of the reference fingerprints, at least initially, but rather the indexing provides a more efficient approach to determining whether there is a match.

The step of determining index values for the reference fingerprints and the sample fingerprint preferably comprises determining same based upon ridge flow curvature of the fingerprints. More particularly, the step of determining the index values may preferably comprise determining curliness index values. The curliness index values may be determined by the steps of: determining a center of each fingerprint; selecting a predetermined portion of each fingerprint relative to a center; and calculating an aggregate of the rate of change ridge flow direction vectors for the predetermined portion of each fingerprint. The step of selecting a predetermined portion of the fingerprint may comprise selecting a generally annularly shaped portion of each fingerprint.

According to another aspect of the invention, the step of selecting the first subset of reference fingerprints preferably comprises selecting same based upon an expected confidence value for locating the sample fingerprint in the first subset. For example, a ninety or ninety five percent confidence level could be selected to assure efficient searching.

Yet another important feature of the method according to the invention compares the sample fingerprint to each fingerprint of the first subset by comparing minutiae of the sample fingerprint to minutiae of each fingerprint of the first subset. If the minutiae are sufficiently close as determined by a matching score, a match is determined. If a match is not determined, the method preferably further includes the steps of selecting a second subset of reference fingerprints having a second and wider range of index values relative to the index value of the sample fingerprint, and comparing the sample fingerprint to the additional fingerprints of the second subset. The process could be repeated until a match is found or until the spread of the index values indicated that no match is likely to be found.

Considered in somewhat different terms, the step of determining index values for the reference fingerprints and the sample fingerprint preferably comprises determining such index values to be generally continuous and to be stable for repeated fingerprints of a finger of an individual. In addition, the step of determining or assigning the indexes preferably comprises determining and sorting the indexes to be a generally monotonically varying function over the reference fingerprints. The step of determining index values for the reference fingerprints and the sample fingerprint preferably comprises determining such index values to be generally incrementally changing in relation to degradation of a fingerprint quality. Accordingly, the index will vary only by a relatively small amount if the fingerprint is slightly degraded. Thus, the indexing and searching method according to the present invention is highly advantageous where fingerprints may be slightly degraded, as may typically be the case.

The invention also results in index values that are preferably generally independent of fingerprint orientation, position and scaling. In addition, the step of determining index values for the reference fingerprints and the sample fingerprint preferably comprises determining such index values to be calculatable from fingerprint information developed for the comparing step. For example, where fingerprint minutiae are used in the comparing step, processing for extraction of the minutiae may also produce the ridge flow curvature data used in accordance with one embodiment of the invention.

The index values according to the method may be one dimensional, but two or more dimensional indexing schemes are also possible. The step of comparing may preferably comprise comparing the sample fingerprint to the reference fingerprints in the first subset based upon fingerprint characteristics independent of ridge flow or other characteristics used for the indexing.

An apparatus according to the present invention may be implemented on one or more processors or computers operating under stored program control. The apparatus is for indexing and searching a plurality of reference fingerprints to determine if a sample fingerprint matches one of the reference fingerprints. In one embodiment, the apparatus preferably comprises indexing means for determining respective index values for the reference fingerprints and the sample fingerprint based upon at least one predetermined fingerprint characteristic and with the index values being generally evenly distributed over a relatively large population of individuals. The apparatus also preferably includes selecting means for selecting a first subset of the reference fingerprints having index values within a first range relative to the index value of the sample fingerprint, and comparing means for comparing the sample fingerprint to each fingerprint of the first subset of reference fingerprints to thereby determine if there is a match between the sample fingerprint and one of the reference fingerprints and without initially requiring comparing of the sample fingerprint to all of the reference fingerprints.

The indexing means preferably includes means for determining and sorting index values for the reference fingerprints and the sample fingerprint to be: monotonically varying and generally continuous over the relatively large population of individuals, generally stable for repeated fingerprints of a finger of an individual, generally incrementally changing in relation to degradation of a fingerprint, calculatable from information developed by or for the comparing means, and/or generally independent of fingerprint orientation, position and scaling.

The selecting means may comprise means for selecting a first subset of reference fingerprints based upon an expected confidence value for locating the sample fingerprint in the first subset. The comparing means may preferably include means for comparing minutiae of the sample fingerprint to minutiae of each fingerprint of the first subset. The selecting means may further comprise means for selecting a second subset of reference fingerprints having a wider range of index values relative to the index value of the sample fingerprint if a match is not found in comparing to the first subset of fingerprints.

The indexing means may include means for determining curliness index values for the reference fingerprints and the sample fingerprint based upon ridge flows of the fingerprints. More particularly, the indexing means may comprise: center determining means for determining a center of each fingerprint, portion selecting means for selecting a predetermined portion of the fingerprint relative to the center, and calculating means for calculating an aggregate of a rate of change of ridge direction vectors for the predetermined portion of the fingerprint.

BRIEF DESCRIPTION OF THE DRAWINGS

FIG. 1 is a schematic block diagram of an embodiment of the apparatus in accordance with the invention.

FIG. 2 is a schematic block diagram of a portion of another embodiment of the apparatus in accordance with the invention.

FIG. 7 is a plot of ridge flow direction vectors and their horizontal component for a sample fingerprint.

FIG. 8 is a plot of ridge flow direction vectors and their vertical component for a sample fingerprint.

FIG. 9 is a plot of ridge flow direction vectors and their total ridge flow components for a sample fingerprint.

DETAILED DESCRIPTION OF THE PREFERRED EMBODIMENTS

Figure 3:
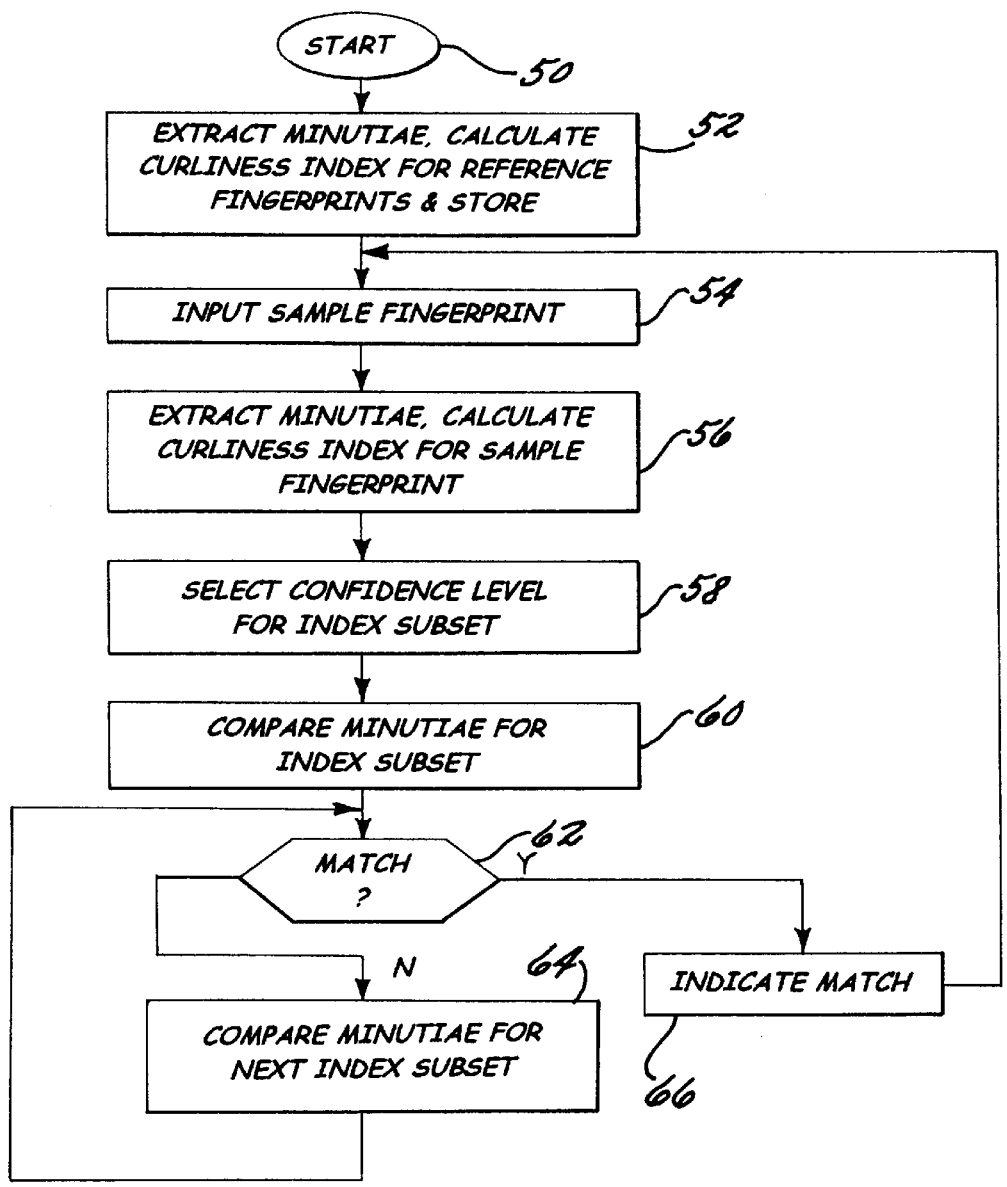
FIG. 3 is a flow chart illustrating a portion of the method in accordance with the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Referring now first to FIGS. 1 and 2, the invention is first described. The apparatus 20 of FIG. 1 includes a fingerprint scanner or sensor 22 for inputting an image of a fingerprint. A suitable fingerprint sensor 22 of an electric field measuring type is described in a copending patent application entitled "*Electric Field Fingerprint Sensor and Related Methods*" having attorney work docket number 16871, Ser. No. 08/592,469, assigned to the assignee of the present invention and the entire disclosure of which is incorporated herein by reference in its entirety. Optical, ultrasonic and other type fingerprint sensors may also be used as would be readily understood by those skilled in the art. In addition, the fingerprint image may be input from a paper copy or transparency of a fingerprint as would also be readily understood by those skilled in the art.

The fingerprint image is processed by the illustrated minutiae extractor 23 and curliness indexor 24 as will be explained in greater detail below. A plurality of reference fingerprints are indexed and stored in the illustrated database 25. The indexed minutiae data from the database 25 may be selectively searched by the illustrated minutiae comparor 27. The illustrated confidence level selector 26 provides the appropriate index range over which to initiate the search. The minutiae comparor 27 may provide a match or no match output as illustrated.

As would be readily understood by those skilled in the art, the output may be used to identify the individual, such as to grant access or permit the person to perform some further function. The match or no match output may also be desirable when determining whether the individual has previously enrolled in the database, such as, for example, to prevent an individual from acquiring multiple driver's licenses under different names. Those of skill in the art will appreciate a wide range of additional applications for the present invention.

Another variation of the apparatus in accordance with the invention is understood with reference to FIG. 2 wherein the apparatus 30 includes a plurality of parallel processors 31a–31n arranged in cooperating relation as would be readily understood by those skilled in the art. The processors 31a–n may be assigned particular index ranges for searching so that overall efficiency and operating speed of the apparatus 30 can be increased over conventional classification based searching approaches when used alone. Those of skill in the art will recognize many applications for the present invention and will further appreciate that the present invention may advantageously be used in combination with one or more of the general conventional fingerprint classification approaches.

Figure 4:
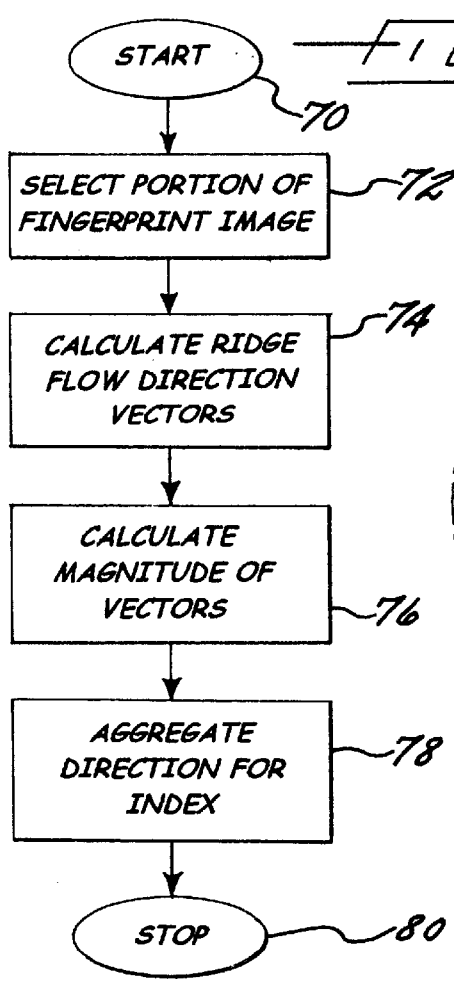
FIG. 4 is a flow chart illustrating another portion of the method in accordance with the present invention.

The overall operation of the invention is additionally understood with particular reference to the flow charts of FIGS. 3 and 4. From the start (Block 50) the fingerprint minutiae is extracted, the curliness index is calculated for each of the reference fingerprints in the database, and the results are stored at Block 52. Alternately, or in addition thereto, a digitized image of each of the reference fingerprints may also be stored for later searching; however, the images are desirably stored with the associated curliness index or other searching index as described in greater detail herein.

As illustrated in Block 54 an input or sample fingerprint is obtained. The minutiae is extracted and the curliness index is calculated for the sample fingerprint at Block 56. A confidence level may be selected for the first range of index values desired to be searched at Block 58. For example, the user may select the confidence level based upon a tradeoff between a likelihood of finding a match and the time of expense for the search. Accordingly, the first range of index values may represent a spread of index values centered about or otherwise related to the sample fingerprint index value. Further, for a relatively large database, the range may be only the index value of the sample fingerprint.

At Block 60 the minutiae of the first subset of the reference fingerprints is compared to the input or sample fingerprint to determine if there is a match at Block 62. A match may be determined, for example, if a minutiae matching score is within a predetermined user selected range. Such minutiae matching is widely used in other conventional fingerprint searching applications as would be readily understood by those skilled in the art, and needs no further discussion herein.

If a match is determined at Block 62, a match may be indicated at Block 66 and the process repeated for another search. If no match is found at Block 62, a second subset including a wider range of index values may be selected for further searching as indicated at Block 64. Because of the desirable characteristics of the index in accordance with the present invention, adjacent indexes are more likely to produce a match than are remote indexes.

Figure 5:
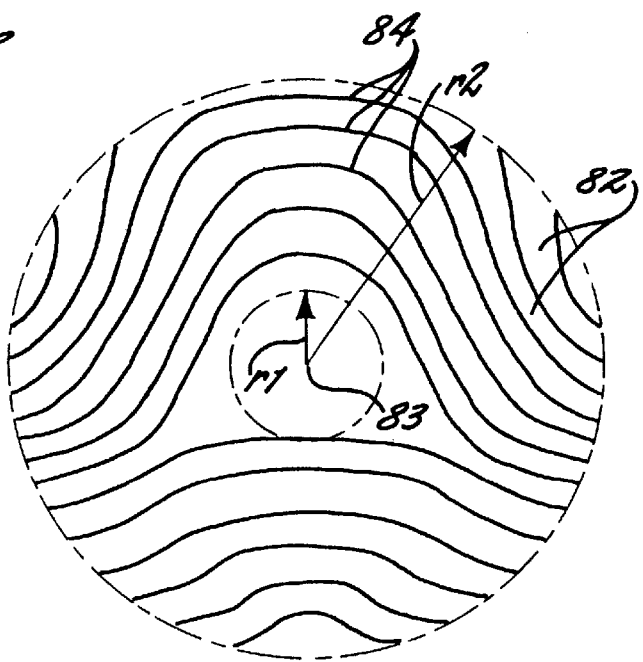
FIG. 5 is a schematic plan view of the fingerprint portion as may be used in accordance with an embodiment of the present invention.
Figure 6:
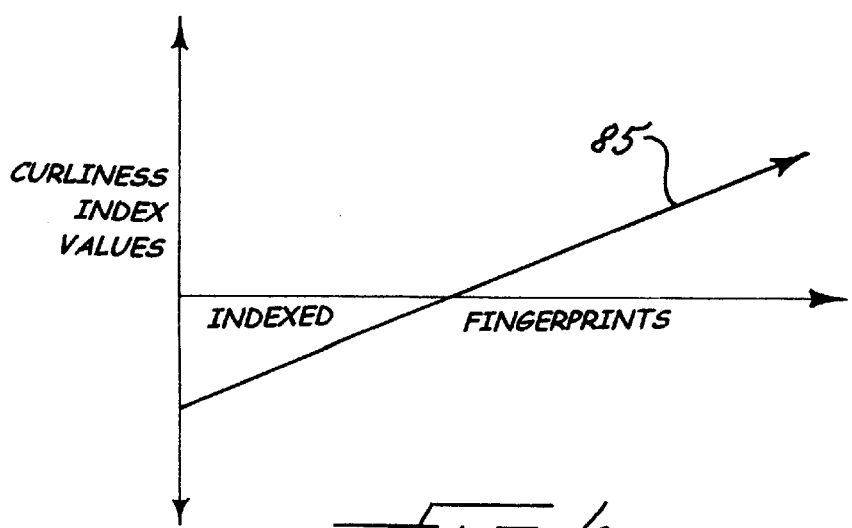
FIG. 6 is a schematic theoretical plot of curliness index values in accordance with an embodiment of the present invention.

Turning now more specifically to the flow chart of FIG. 4, and the diagrams of FIGS. 5 and 6, the curliness index in accordance with one embodiment of the present invention is further described. After the start (Block 70) a portion of a fingerprint may be selected at Block 72 for further analysis. As shown in FIG. 5, a generally annularly shaped portion 82 defined by radii r1 and r2 may be selected based upon a center point 83 of the fingerprint ridges 84. The center point 83 of the fingerprints may be readily determined by conventional algorithms and approaches as will be readily appreciated by those skilled in the art. For example, the approaches described in U.S. Pat. No. 5,140,642 to Hsu et al. and U.S. Pat. No. 5,040,224 to Hara may be used to locate the center point and the disclosures of both of these patents are incorporated herein by reference in their entirety.

The ridge flow direction vectors may be calculated at Block 74. The magnitude of the vectors may be optionally calculated at Block 76, and an aggregate of the ridge flow direction vectors calculated at Block 78 to define the curliness index before stopping at Block 80. The curliness index may be considered as somewhat similar to a Reynolds number used in fluid dynamics. A higher value of Reynolds number indicates higher turbulence in the flow of a fluid. Similarly, a higher value of the curliness index would indicate more changes in directions in the ridges, that is, a more turbulent pattern.

Calculation of the curliness index might be represented as follows:

$$\xi = \frac{1}{q} \int \int \Delta\theta(x', y') \partial x \partial y$$

$$r_1^2 \leq x'^2 + y'^2 \leq r_2^2$$

where:
 $\xi$=Curliness Index
 $\theta$=Local Ridge Direction Angle
 $r_1$=Inner Radius of the Evaluation Region
 $r_2$=Outer Radius of the Evaluation Region
 q=fingerprint quality index=percent of evaluation region that contains usable ridge direction data, and
 x' and y' are coordinates normalized to originate at the calculated center of the fingerprint pattern.

Referring now additionally to the schematically illustrated graph of FIG. 6, desirable properties of the curliness index and other similar indexes are further explained. The curliness index when computed for each fingerprint of the database can be used to sort the fingerprints into a monotonically increasing sequence represented by plot 85. The curliness index computed for a sample fingerprint points to the location in the sorted database where the matching print is most likely to be found. It improves the performance of searches by directing those searches to try the most likely areas in which to find a match first. The matcher may start its search at the indicated location in the sorted database. If that print does not match as indicated by failure to meet its predetermined minutiae-match reference score, for example, the matcher tries the prints immediately above and below in the sorted database. In other words, the search may be expanded to a second subset of index is values. This is repeated until a match is found or until the likelihood of a match is so low that further searching is not justified or desired.

The curliness index according to the present invention produces a number of desirable properties for efficient and accurate searching. The present invention also contemplates other indexing schemes as would be readily understood by those skilled in the art. For example, an aggregate of second derivatives of the ridges may be used to compute an index. Alternatively, a pattern of crossings may be generated by respective fingerprints from fingers of the left and right hands of the individual and the crossings may be used as an indexing scheme which has one or more of the desirable characteristics as embodied by the curliness index.

For example, the index values are preferably readily sorted to be define a generally monotonically varying function, are preferably generally continuous and are stable for repeated fingerprints of a finger of an individual. The index values are also desirably generally incrementally changing in relation to degradation of fingerprint quality. Accordingly, the index will vary only by a relatively small amount if the fingerprint is slightly degraded. Thus, the indexing and searching method according to the present invention is highly advantageous where all prints may be slightly degraded, as may typically be the case. In such an instance, the range of index values to be searched as related to the expected confidence value of finding a match can be advantageously selected to thereby account for degradation of the fingerprint.

The index values are also preferably generally independent of fingerprint orientation, position and scaling. Moreover, the index values for the reference fingerprints and the sample fingerprint are preferably calculatable from fingerprint information developed for the comparing step. For example, where fingerprint minutiae are used in the comparing step, processing for extraction of the minutiae may also produce the ridge flow data described above in the curliness index embodiment of the invention. The index values according to the method may be one dimensional, but two or more dimensional indexing schemes are also possible. The step of comparing the sample fingerprint to the reference fingerprints in the first subset may also be based upon fingerprint characteristics independent of ridge flow or other characteristic used for the indexing.

The situation wherein the sample print being searched has a match in the database describes many high-volume identification and authentication applications. In these cases, the user has enrolled himself in the database and expects to be recognized. This is the type of application that may be especially benefitted by the curliness index and other index embodiments in accordance with the present invention. The situation where the search print has no match in the database describes an initial enrollment situation, where the global search is used to identify someone re-enrolling under an alias, and many law enforcement booking applications.

EXAMPLES

The following examples are illustrative of the present invention only and are not intended to be limiting of the invention.

Figure 7:
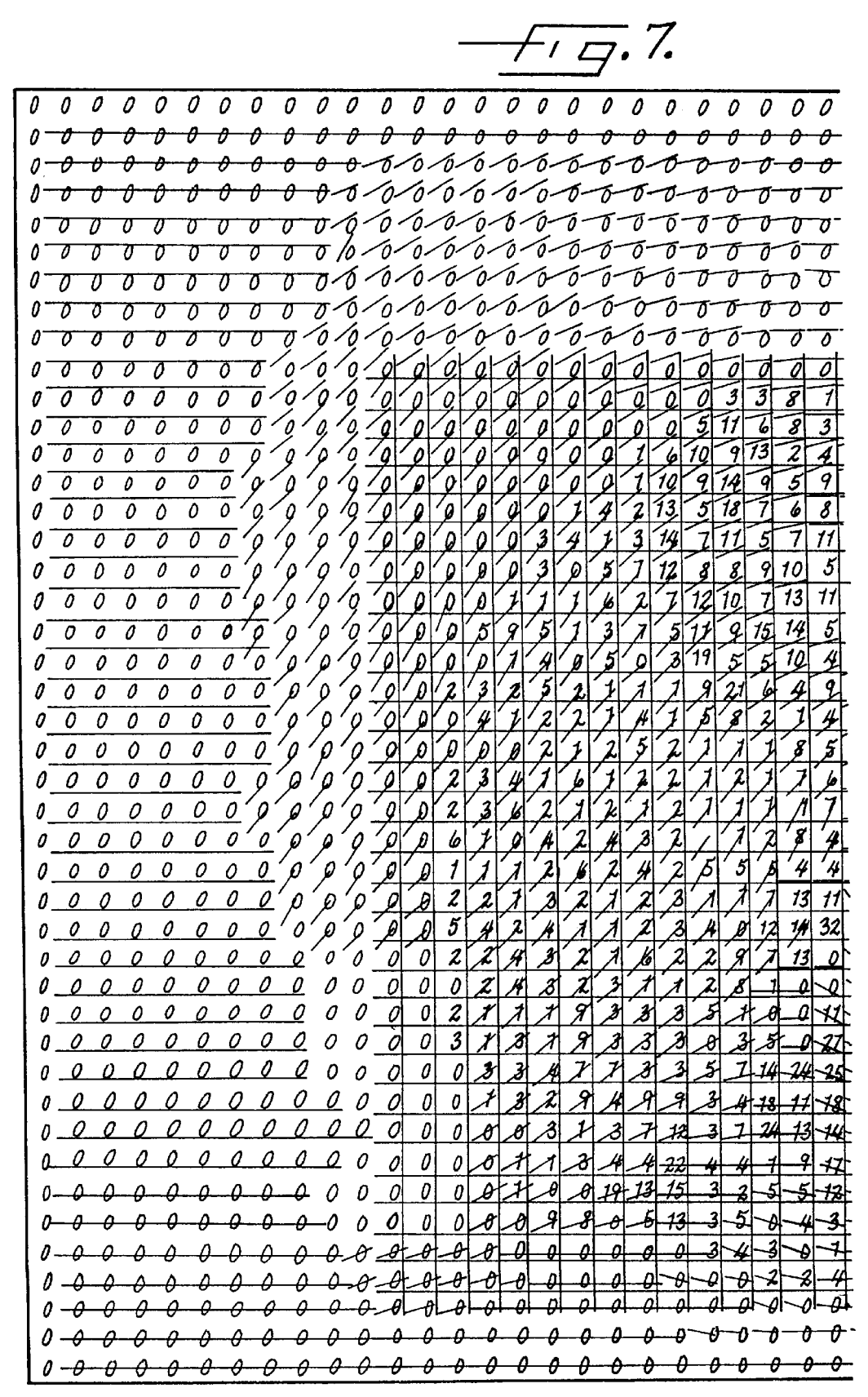
Figure 7:
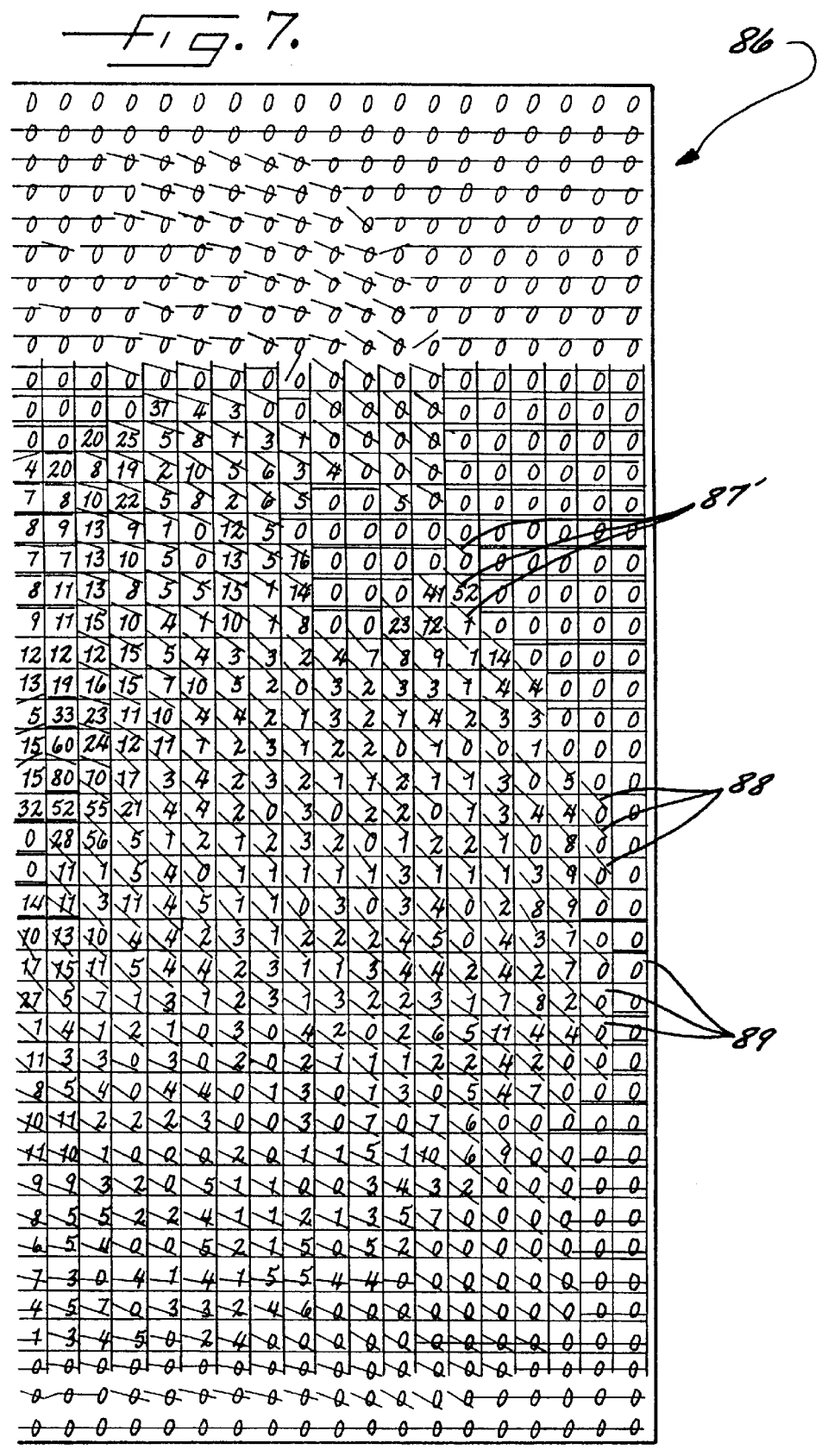
Figure 8:
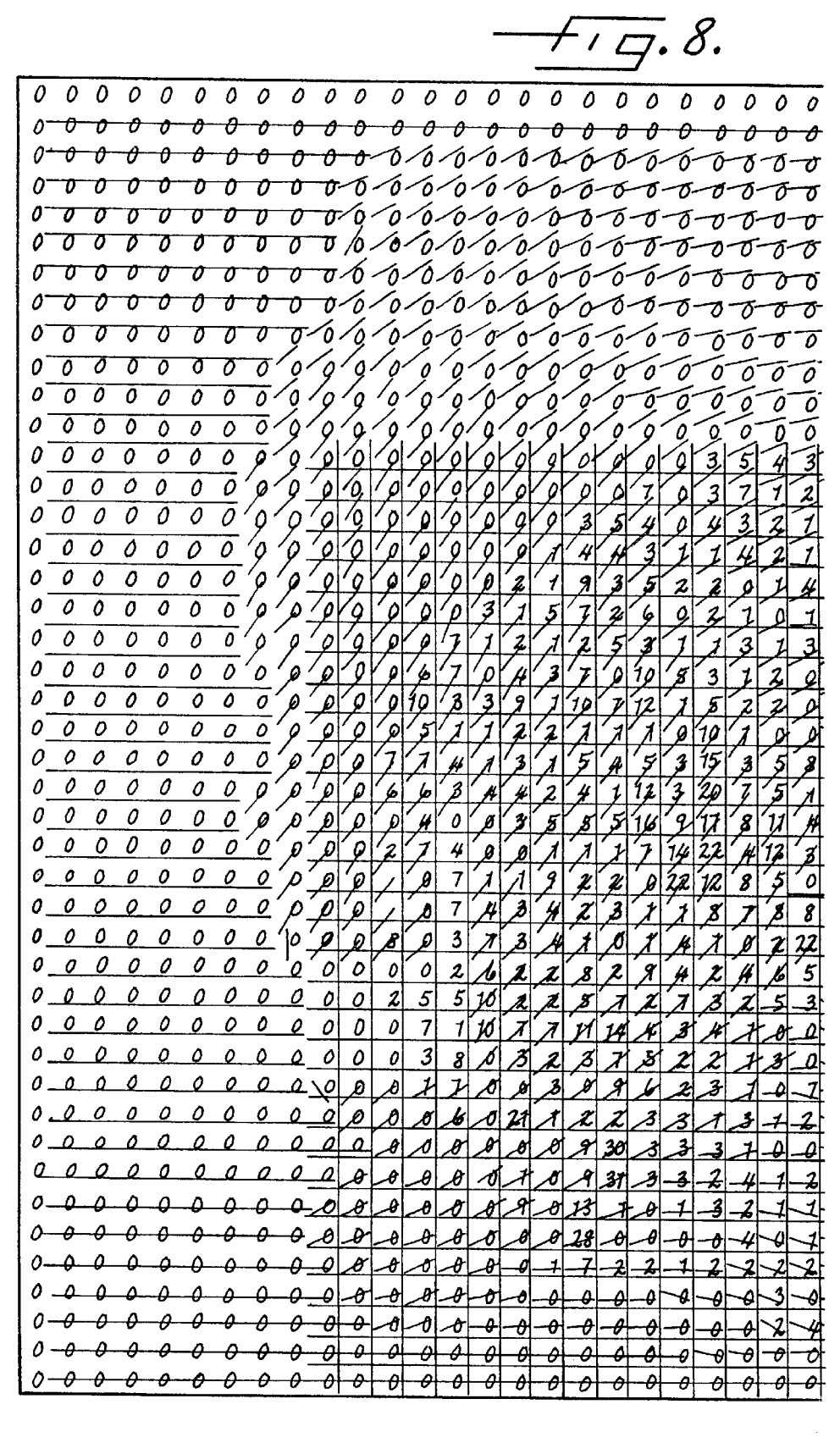
Figure 8:
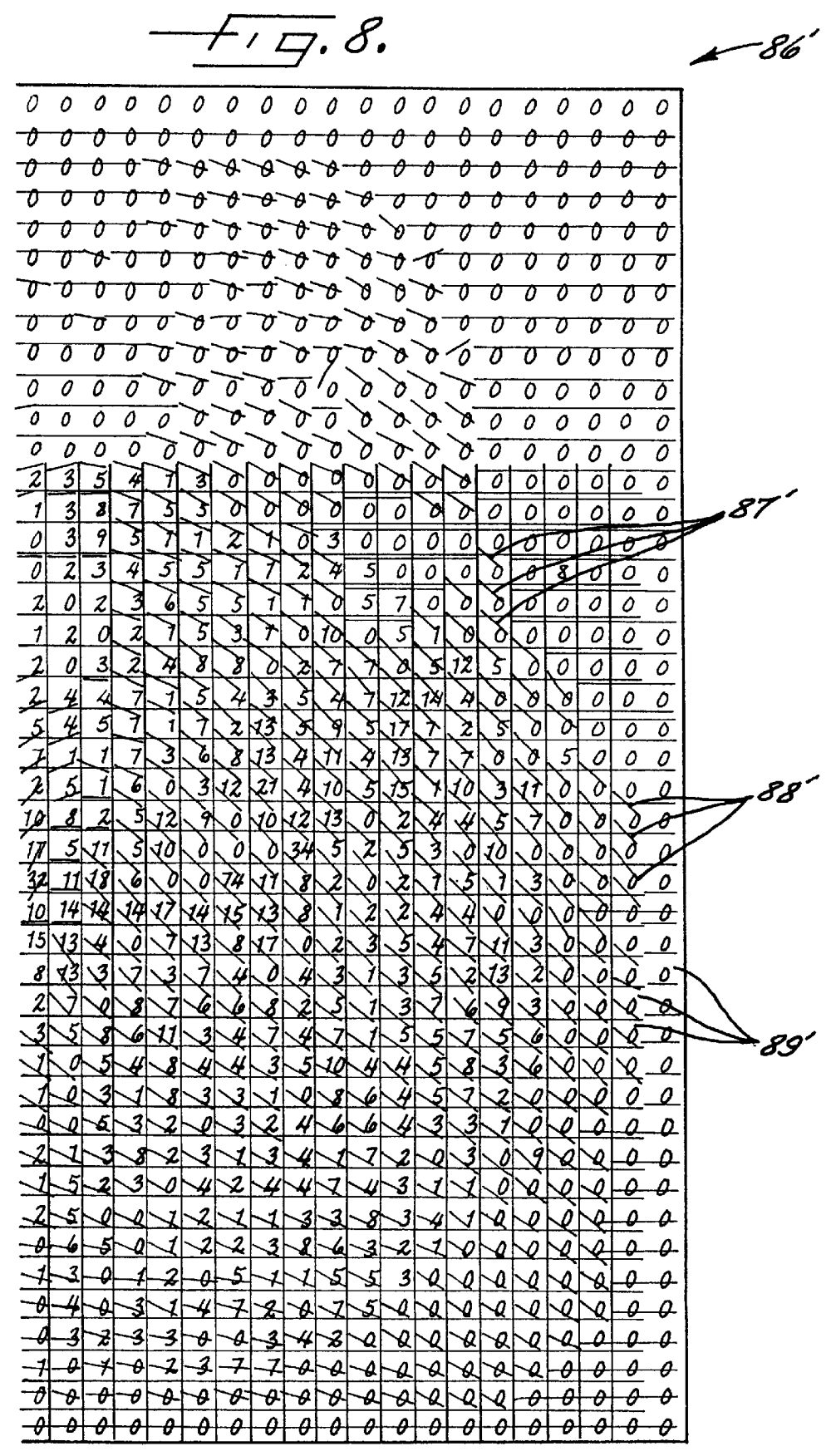
Figure 9:
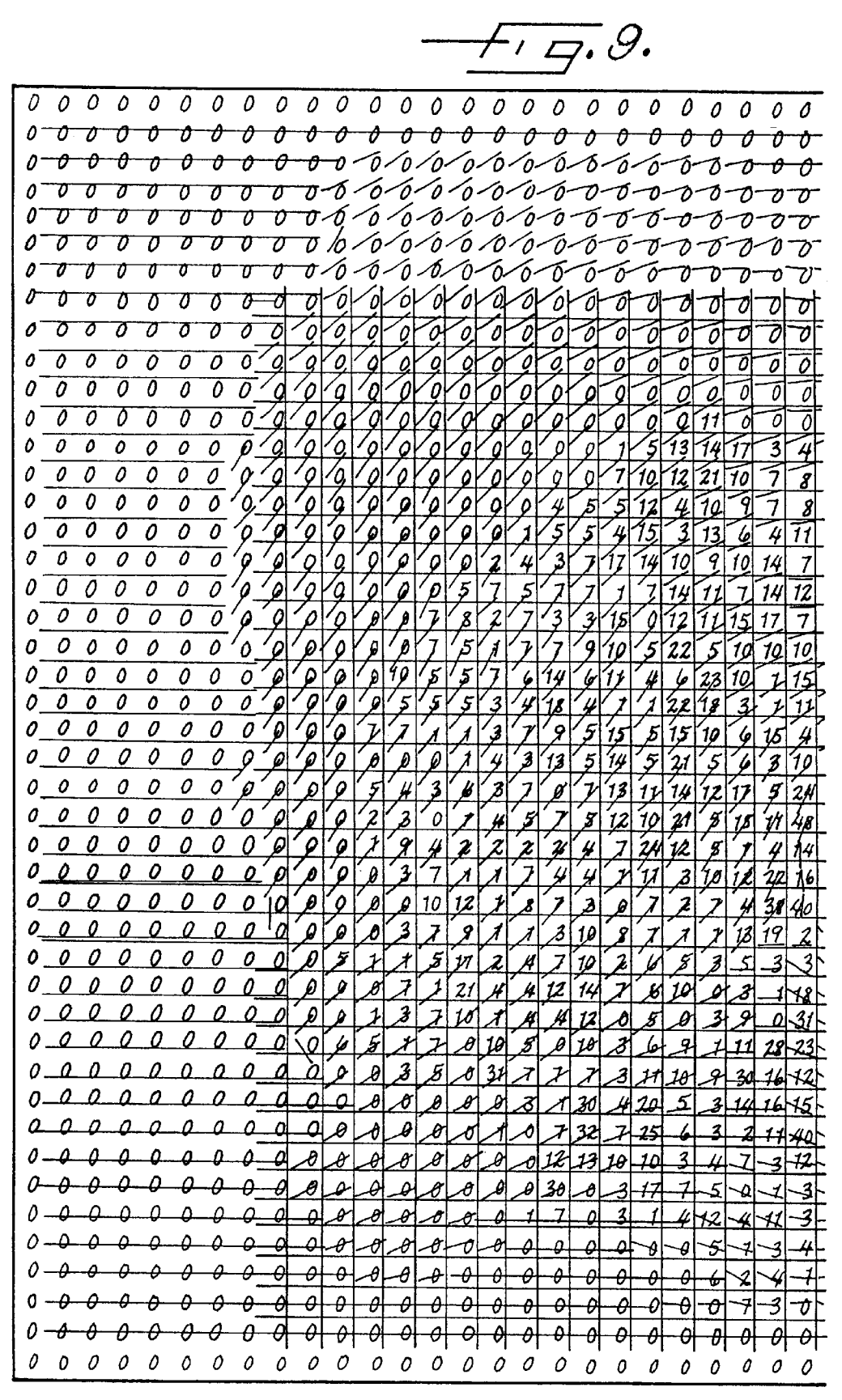
Figure 9:
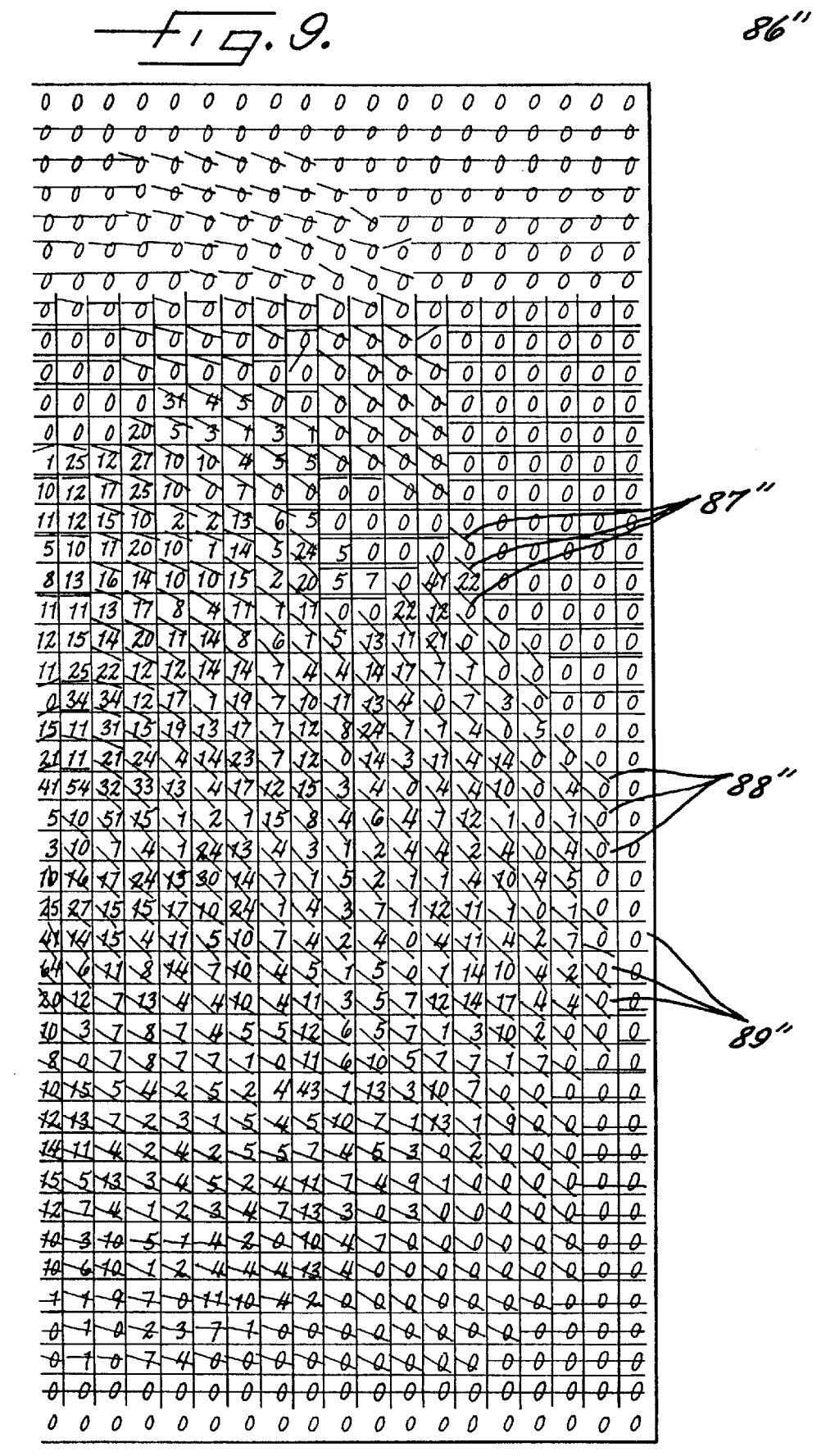

Referring now to FIGS. 7–9 a representative curliness calculation for a sample fingerprint is further explained. In FIG. 7, the ridge flow direction vectors of a sample fingerprint and its horizontal curl component tabulations are illustrated by the matrix 86. The angled lines 87 in each ridge flow cell 89 of the figure illustrate the ridge direction flow. The number 88 in each cell 89 represents the calculated horizontal curl component at that position. Similarly, FIG. 8 illustrates the vertical curl components, and FIG. 9 illustrates a total of both the horizontal and vertical curl components. Prime and double prime notation is used to indicate similar elements in FIGS. 8 and 9, respectively. In these illustrated samples, the center portion of the fingerprint has been used, although as described above, in other embodiments of the invention the area at the center of the fingerprint may not be used.

The results from several tests of the curliness index confirmed that use of the curliness index can improve the performance of fingerprint cold-search operations significantly. The curliness index was tested against two available fingerprint databases to determine the ability of the index to improve the performance of the database searches required for fingerprint matching.

Figure 10:
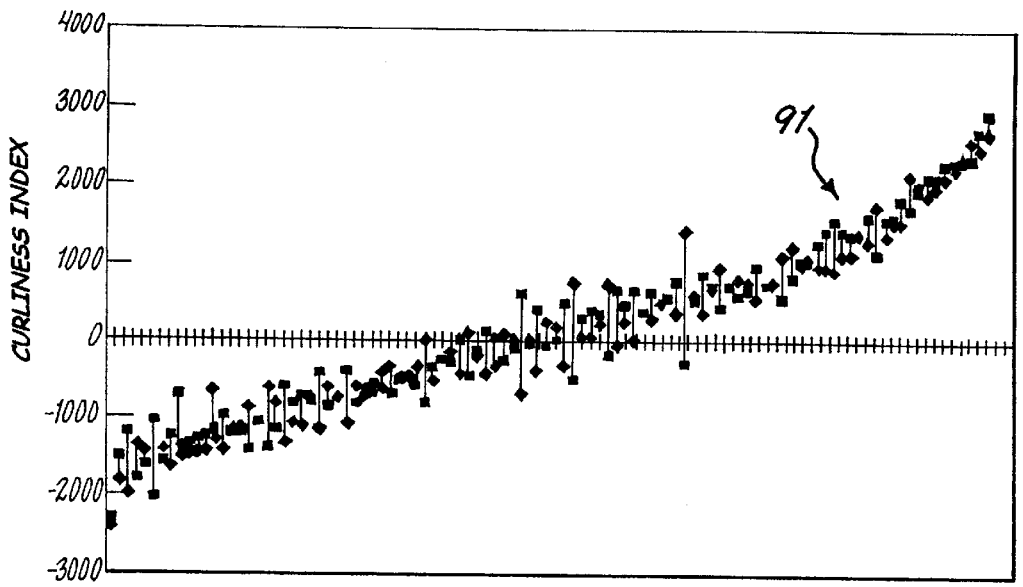
FIGS. 10 and 11 are plots of curliness index values for databases as described in the Examples.

The first database is of live-scan fingerprints from an ultrasonic fingerprint scanner. This database contained data for 103 fingers, with two representative images of each finger illustrated by the squares and diamonds defining the plot 91 of FIG. 10 shown in sorted order based upon an average of the curliness values for each finger. The curliness algorithm was used without ridge flow smoothing and all of the prints have about 5–15% of the ridge flow cells indeterminate. For this first database the performance analysis indicates:

1. 15 to 1 average performance improvement over global search when the search print has a match in the database.
2. 5 to 1 performance improvement over global search for 99% confidence that no match exists.

Figure 11:
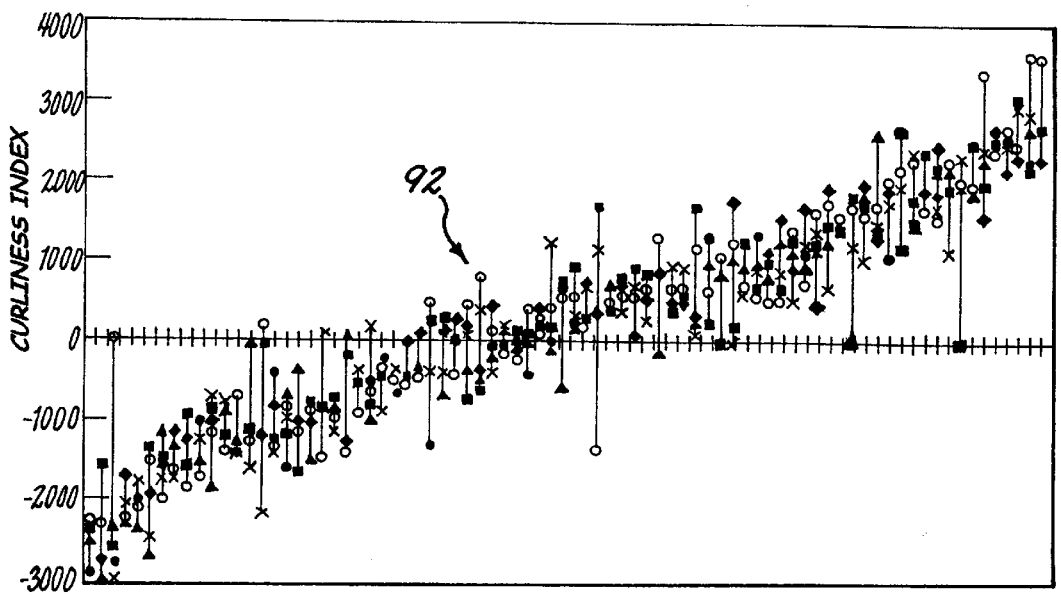

The second database is of live scan fingerprints from 81 fingers with 5 sample images for each. This data is sorted and illustrated by the plot 92 of FIG. 11 with the index values for the five images of each finger represented by respective geometric figures along respective vertical lines. The performance analysis for this database indicates:

1. 10 to 1 average performance improvement over global search when the search print has a match in the database.
2. 3 to 1 performance improvement over global search for 95% confidence that no match exists.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A method for indexing and searching a plurality of data elements of a reference data group from a relatively large, selected population of data to determine if a sample data element matches one of the data elements in the reference data group, the method comprising the steps of:

determining respective full entire index values for each of the plurality of data elements of the reference data group and the sample data element based upon at least one predetermined data element characteristic and with the full entire reference index values being sorted in either a numerically ascending or descending order and substantially evenly distributed over the relatively large population of data;

selecting a first subset having a plurality of data elements of the sorted reference data group, the first subset having index values in a first range relative to the full entire index value of the sample data element, the first subset also having substantially fewer data elements than the reference data group;

comparing the sample data element to each data element of the first subset of the reference data group to thereby determine if there is a match between the sample data element and one of the plurality of data elements of the first subset, of the reference data group; and selecting a second subset having a plurality of sorted data elements of the reference data group if a match is not found in the step of comparing to the first subset of the reference data group, the second subset having a second expanded range of full entire index values larger than the first range so that the second expanded range extends at least immediately above and below the first range.

2. A method according to claim 1, wherein the step of determining index values for each of the plurality of data elements of the reference data group and the sample data element comprise determining and sorting such index values to be a generally monotonically varying function over the relatively large population of data.

3. A method according to claim 1, wherein the step of determining index values for each of the plurality of data elements of the reference data group and the sample data group comprises determining such index values to be generally continuous over the relatively large population of individuals.

4. A method according to claim 1, wherein the step of determining index values for each of the plurality of data elements of the reference data group and the sample data element comprises determining such index values to be generally stable for repeated data elements of a data group.

5. A method according to claim 1, wherein the step of determining index values for each of the plurality of data elements of the reference data group and the sample data element comprises determining such index values to be generally incrementally changing in relation to degradation in quality of a data element.

6. A method according to claim 1, wherein the step of determining index values for the reference data elements and the sample data element comprises determining such index values to be generally independent of data element orientation, position and scaling.

7. A method according to claim 1, wherein the step of selecting a first subset of the reference data group comprises selecting same based upon an expected confidence value for locating the sample data element in the first subset of the reference data group.

8. A method according to claim 1, wherein the step of comparing the sample data element to each data element of the first subset of the reference data group comprises comparing minutiae of the sample data element to minutiae of each data element of the first subset of the reference data group.

9. A method according to claim 1, wherein the step of determining index values for the reference data elements and the sample data elements comprises determining such index values based upon preselected characteristics of the data elements.

10. A method for searching a plurality of reference data elements to determine if a sample data element matches one of the reference data elements, each of the reference data elements having associated therewith a full entire index value based upon at least one predetermined data element characteristic and with the full entire index values for the reference data elements being sorted in either a numerically ascending or desending order and substantially evenly distributed over a relatively large population of individuals, the method comprising the steps of:

determining a full entire index value for the sample data element based upon the at least one predetermined data element characteristic;

selecting a first subset having a plurality of data elements of the sorted reference data elements, the first subset having full entire index values in a first range relative to the full entire index value of the sample data element, the first subset also having substantially fewer data elements than the plurality of reference data elements;

comparing the sample data element to each data element of the first subset of reference data elements to thereby determine if there is a match between the sample data element and one of the plurality of data elements of the first subset of the reference data elements; and selecting a second subset having a plurality of data elements of the sorted reference data group if a match is not found in the step of comparing to the first subset of the reference data elements, the second subset having a second expanded range of full entire index values larger than the first range so that the second expanded range extends at least immediately above and below the first range.

11. A method according to claim 10, wherein the step of selecting a first subset of the reference data elements comprises selecting same based upon an expected confidence value for locating the sample data element in the first subset of reference data elements.

12. A method according to claim 10, wherein the step of determining a full entire index value for the sample data element comprises determining such a full entire index value based upon a plurality of preselected characteristics of the sample data element.

13. A method according to claim 10, wherein the step of determining a full entire index value for the sample data element comprises the steps of:

determining a predefined region of the sample data element;

selecting a predetermined portion of the sample data element relative to the predefined region; and calculating an aggregate of a rate of change of direction vectors for the predetermined portion of the sample data element.

* * * * *